United States Patent [19]

Hyoda et al.

[11] Patent Number: 5,618,978

[45] Date of Patent: Apr. 8, 1997

[54] METHOD OF PRODUCING CHOLINE OF A HIGH PURITY

[75] Inventors: Shunji Hyoda; Youichi Hasegawa, both of Marugame; Fumio Toda, Shigenobu, all of Japan

[73] Assignee: Japan Hydrazine Co., Ltd., Tokyo, Japan

[21] Appl. No.: 622,082

[22] Filed: Mar. 26, 1996

[51] Int. Cl.$^6$ .................................................. C07C 209/84
[52] U.S. Cl. ........................................... 564/293; 564/296
[58] Field of Search ...................................... 564/293, 296

[56] References Cited

U.S. PATENT DOCUMENTS 2,774,759  12/1956  Blackett et al. ...................... 260/251.5

Primary Examiner—Peter O'Sullivan
Attorney, Agent, or Firm—Robbins, Berliner & Carson, LLP

[57] ABSTRACT

A method of producing a choline having a high purity without containing by-products by using a molecule-inclusion complex of the choline as a starting material. A choline inclusion complex without containing by-products is obtained by reacting an aqueous solution of the choline containing, as by-products, those cholines to which are added ethylene oxides with host molecules such as of 1,1'-bis-β-naphthol, and is further reacted with a carbon dioxide gas in order to obtain an aqueous solution of a choline carbonate and/or a choline bicarbonate of a high purity, which is then subjected to the electrolysis using a cation-exchange membrane as a diaphragm, in order to obtain an aqueous solution of the choline of a high purity without containing by-products. The choline that is obtained is a strongly basic compound having a high purity and is very useful as a photoresist-developing solution.

5 Claims, No Drawings

METHOD OF PRODUCING CHOLINE OF A HIGH PURITY

BACKGROUND OF THE INVENTION

1. Field of the Invention

The present invention relates to a method of producing a choline of a high purity. More specifically, the invention relates to a method of producing a choline of a high purity using, as a starting material, a molecule-inclusion complex of the choline passing through a choline carbonate and/or a choline bicarbonate.

2. Prior Art

A choline is a strongly basic substance and is used as a photoresist-developing solution. It is, however, difficult to remove by-products formed during the production of a chlorine. So far, therefore, the choline has been used in the presence of by-products thereof.

The choline is usually prepared in compliance with the following reaction formula (1),

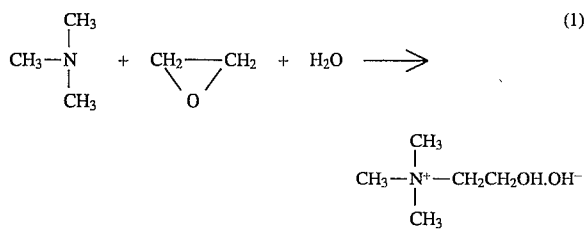

This is the addition reaction in which an ethylene oxide is added to a trimethylamine, and it is estimated that the compounds of the following formula (2) are formed as by-products,

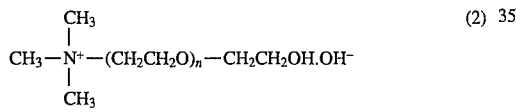

These by-products are the ones in which the ethylene oxides are successively added to the choline and, wherein n is chiefly 1 or 2. A conventional aqueous solution of the choline contains the above-mentioned by-products in amounts of from about 2 to about 3% by weight with respect to the choline.

The present inventors have already proposed a method by which a quaternary ammonium hydroxide and/or a salt thereof forms an inclusion complex with particular phenols (Japanese Patent Application No. 38894/1994) and a method by which choline, too, forms a similar molecule-inclusion complex which reacts with a carbon dioxide gas to form a choline carbonate and/or a choline bicarbonate (Japanese Patent Application No. 255760/1994).

It is virtually difficult to suppress the formation of, or to remove, by-products contained in the choline relying upon a generally employed chemical or physical treatment such as improving the reaction conditions for the choline, distillation, recrystallization or adsorption. If a highly pure choline could be produced without containing by-products, a further extended application is expected as a photoresist-developing solution and, besides, new applications can be explored in the fields of medicine, agricultural chemicals and functional materials.

SUMMARY OF THE INVENTION

The present inventors have discovered the fact that impurities contained in the choline can be removed by using a molecule-inclusion complex of the choline as a starting material and that the choline of a high purity can be produced by subjecting a choline carbonate and/or a choline bicarbonate obtained by reacting the molecule-inclusion complex with a carbon dioxide gas to the electrolysis using a cation-exchange membrane as a diaphragm.

That is, the object of the present invention is to provide a method of producing a choline of a high purity without containing by-products by using a molecule-inclusion complex of the choline as a starting material.

According to the present invention, there is provided a method of producing a choline of a high purity, wherein a choline carbonate and/or a choline bicarbonate of a high purity obtained by reacting a molecule-inclusion complex of the chlorine with a carbon dioxide gas, is subjected to an electrolysis using a cation-exchange membrane as a diaphragm.

According to the present invention, furthermore, there is provided a method of producing a choline of a high purity, wherein an aqueous solution of the choline containing by-products is reacted with 1,1'-bis-β-naphthol, and a molecule-inclusion complex of the choline that is formed is reacted with a carbon dioxide gas to form a choline carbonate and/or a choline bicarbonate of a high purity, which is then subjected to the electrolysis using a cation-exchange membrane as a diaphragm.

When a given compound takes in another compound to form a complex, this complex is called molecule-inclusion compound, the former compound is called host molecule and the latter compound is called guest molecule.

The present invention is based upon a novel discovery that the choline only in an aqueous solution of the choline forms a molecule-inclusion complex with host molecules such as of 1,1'-bis-β-naphthol but does not form a molecule-inclusion complex with by-products. That is, the aqueous solution of the chlorine is reacted with host molecule such as of 1,1'-bis-β-naphthol to form a choline-inclusion complex without containing by-products which is then dispersed in water followed by the blow of a carbon dioxide gas to obtain a choline carbonate and/or a choline bicarbonate of a high purity in the form of an aqueous solution, which is, then, subjected to the electrolysis using a cation-exchange membrane as a diaphragm to obtain a choline in a highly pure form.

That is, the choline taken in by the choline-inclusion complex reacts with the carbon dioxide gas to form a water-soluble choline carbonate and/or choline bicarbonate which is then dissolved in water to obtain the choline carbonate and/or the choline bicarbonate of a high purity in the form of an aqueous solution. The reaction is expressed by the following formulas (3), (4) and (5),

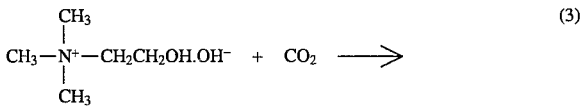

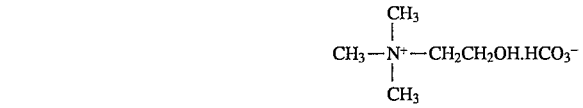

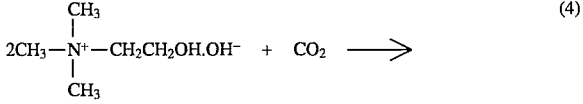

3
-continued

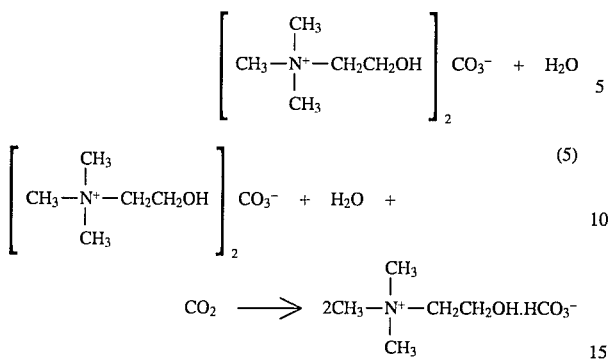

The aqueous solution of the thus obtained choline carbonate and/or choline bicarbonate of a high purity is subjected to the electrolysis using a cation-exchange membrane as a diaphragm to obtain the choline of a high purity in the form of an aqueous solution. The reaction is expressed by the formula (6) or (7),

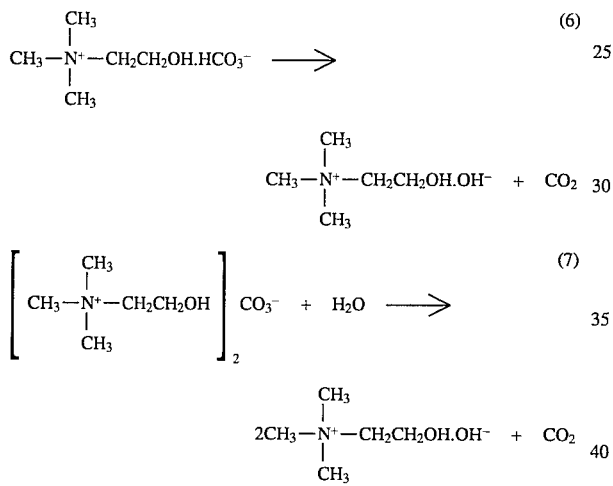

The present invention uses the molecule-inclusion complex of the choline, which does not at all contain by-products represented by the above-mentioned formula (2), as a starting material. Besides, by reacting the molecule-inclusion complex with a carbon dioxide gas, it becomes possible to take out the choline in the molecule-inclusion complex as the choline carbonate or the choline bicarbonate of a high purity. By subjecting the choline carbonate or the choline bicarbonate of a high purity to the electrolysis, furthermore, it is made possible to obtain the choline in a very highly pure form. That is, anionic moieties forming a choline salt are a carbonate and/or a bicarbonate anion that turn into a volatile carbon dioxide gas through the electrolysis using a diaphragm. Accordingly, the choline product features a very high purity.

DETAILED DESCRIPTION OF THE EMBODIMENT

Examples of the host compound that can be used in the present invention are the phenol compounds disclosed in, for example, Japanese Patent Publication No. 21017/1994; i.e.,

4

(i) phenol compounds of the formulas,

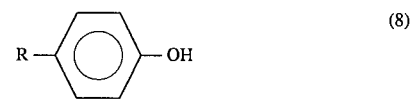

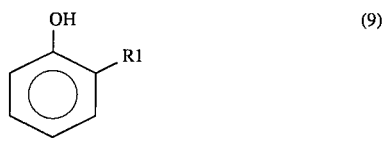

wherein R is a hydrogen atom, an alkyl or alkoxyl group with 1 to 3 carbon atoms, or a phenyl group, and R1 is an alkoxyl group with 1 to 3 carbon atoms, (ii) dihydroxybenzene compounds of the formulas,

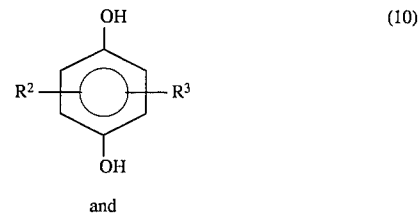

and

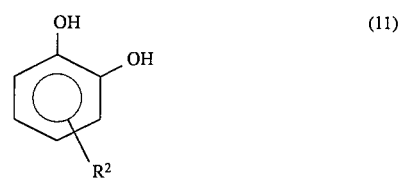

wherein R2 and R3 are each a hydrogen atom, a lower alkyl group, or a phenyl group substituted with a lower alkyl, or R2 and R3 in combination form a group of the formula,

(iii) bisphenol compounds of the formula

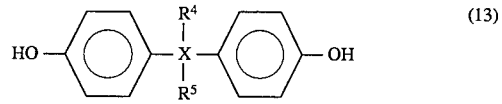

wherein X is a sulfur atom or a carbon atom, and when X is a sulfur atom, R4 and R5 are both oxygen atoms and when X is a carbon atom, R4 and R5 are each a hydrogen atom, a lower alkyl group or a phenyl group, or R4 and R5 in combination form a cyclohexyl group together with X, and (iv) naphthols.

Among them, a particularly preferred example is a 1,1'-bis-β-naphthol, i.e., a compound of the following formula (14),

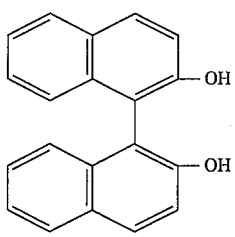

(14)

The guest compound that is used in the present invention is a choline. An aqueous solution of the choline prepared by the method of the above-mentioned reaction formula (1) can be used as a starting material.

According to the present invention, the choline of a high purity is produced by a method described below.

A 1,1'bis-β-naphthol and an aqueous solution of choline are fed at a ratio of 1,1'-bis-β-naphthol/choline=1/1 or 1/2 (molar ratio) into a reactor together with pure water, and are heated and dissolved.

An aqueous solution of the choline that is to be used is prepared by the method of the formula (1), and contains by-products of the above-mentioned general formula (2) in amounts of several percent by weight with respect to the choline.

After heated and dissolved, crystals of the molecule-inclusion complex of the 1,1'-bis-β-naphthol and the choline readily precipitate. After stirred for about one hour, the aqueous solution of the choline is cooled down to room temperature, subjected to the filtration or centrifugation, followed by washing with water and drying, in order to obtain a highly pure molecule-inclusion complex without containing by-products maintaining an yield as high as not smaller than 80 mol % .

Pure water is added to the obtained molecule-inclusion complex of a high purity and a carbon dioxide gas is blown thereto. Then, the 1,1'-bis-β-naphthol is removed as insoluble crystals by the filtration or centrifugation, in order to obtain an aqueous solution of the choline carbonate and/or the choline bicarbonate having high purity without containing by-products.

This aqueous solution does not contain 1,1'-bis-naphthol of the host compound.

The recovered 1,1'bis-β-naphthol is reusable, and its recovery rate is nearly quantitative.

The thus obtained aqueous solution of the choline carbonate and/or the choline bicarbonate of a high purity is subjected to the electrolysis using a cation-exchange membrane as a diaphragm in order to obtain the choline having a high purity.

The electrolysis of the present invention uses a general electrolytic cell which is sectionalized into an anode chamber and a cathode chamber by a cation-exchange membrane. There is no particular limitation on the type of the electrolytic cell.

The cation-exchange membrane used in the present invention is a widely-known one having cation-exchange groups such as sulfonic acid group, carboxylic acid group or phosphonic acid group. Preferably, there is used a cation-exchange membrane having a fluorine-containing resin as a skeleton. Preferably, there is used a cation-exchange membrane of the sulfonic acid type such as Nafion 966 or 350 (manufactured by Du Pont Co.) of the type of fluorine-containing resin.

As the anode of the present invention, there can be used an electrode obtained by depositing a film containing a metal of the platinum group or an oxide thereof on a corrosion-resistant substrate, or an electrode exhibiting a large corrosion resistance in an oxidizing atmosphere, such as magnetite. As the cathode of the present invention, there can be used a metal that is not corroded with an alkali, such as a stainless steel or nickel. The anode and the cathode may be used in any shape such as plate, rod, net, or porous plate.

In the present invention, the electrolysis is carried out by feeding the aqueous solution of the choline carbonate and/or the choline bicarbonate of a high purity into the anode chamber in the electrolytic cell, feeding ultra-pure water into the cathode chamber, and applying a DC voltage across the two electrodes. Here, the current density is from 1 to 100 $A/dm^2$ and, preferably, from 3 to 50 $A/dm^2$.

In the present invention, it is desired that the electrolysis is carried out at a temperature of from 10° to 50° C.

In the present invention, the electrolysis is carried out either batchwisely or continuously.

In the present invention, the starting material is fed to the anode chamber at a concentration of from 1 to 60% by weight and, preferably, from 3 to 40% by weight.

In the present invention, ultra-pure water is fed to the cathode chamber. At the start of the electrolysis, however, the electric conductivity of pure water is so low that the electrolysis takes place little. It is therefore desired to use a solution to which has been added the desired choline of a high purity in a small amount, for example, in an amount of from about 0.01 to about 5% by weight.

In the present invention, it is desired that the electrolysis is carried out in an atmosphere of an inert gas such as clean nitrogen or argon.

According to the present invention as described above, the choline of a high purity is obtained by electrolyzing the aqueous solution of the choline carbonate and/or the choline bicarbonate of a high purity.

EXAMPLE

The invention will now be concretely described by way of Example to which only, however, the invention is in no way limited.

Example 1

143.17 Grams (0.50 mols) of a 1,1'-bis-β-naphthol and 253.30 g of an aqueous solution containing 47.84% by weight of the choline (1.00 mol) were added to 1,207 g of pure water, and were heated and dissolved. The amount of by-products in the aqueous solution of the choline was 1.85% by weight with respect to the choline. After heated and dissolved, crystals precipitated immediately. The aqueous solution of the choline was heated and stirred at 50° C. for one hour, and was then cooled, subjected to the filtration or centrifugation, followed by washing with water. The obtained crystals were further washed with water under stirred and filtered three times. After drying, there was obtained 1,1'-bis-β-naphthol/choline inclusion complex in an amount of 171.90 g (0.42 mols). The yield was 84.40 mol %. By the NMR analysis, the molecular ratio of the inclusion complex was 1,1'-bis-β-naphthol/choline =1/1. The choline in the inclusion complex was subjected to the ionic chromatography, and it was learned that the amounts of by-products were smaller than a detectable limit.

171.90 Grams (0.42 mols) of the obtained inclusion complex without containing by-products was added to 1,000 g of pure water, and a carbon dioxide gas was blown thereto with stirring at room temperature for one hour.

The obtained solution was filtered and washed with water and insoluble crystals were obtained as a residue. This washing and filtration, further, was carried out two times to obtain, as total amounts of filtrates, 2,654.50 g of an aqueous solution containing 2.29% by weight of the choline carbonate or the choline bicarbonate of a high purity (60.79 g as the choline bicarbonate). The yield was 87.62 mol %.

After drying, the insoluble crystals were recovered in an amount of 120.25 g (0.42 mols). By the IR analysis, it was confirmed that the insoluble crystals were 1,1'-bis-β-naphthol. The yield was 100%.

The aqueous solution containing 2.29% by weight of the choline carbonate and/or the choline bicarbonate of a high purity obtained as the mother liquor was condensed under reduced-.pressure to obtain an aqueous solution containing 18.85% by weight of the same compound, which was then subjected to the next electrolytic reaction.

There was used an electrolytic cell having a pair of anode and cathode each with an effective area of $2.89 \times 10^{-2}$ $dm^2$. The electrolytic cell was sectionalized into an anode chamber and a cathode chamber using Nafion 350 (produced by Du Pont Co.) which was the cation-exchange membrane of the type of fluorine-containing resin. In the anode chamber of the electrolytic cell was provided an anode composed of platinum and in the cathode chamber was provided a cathode composed of a stainless steel.

Into the anode chamber was fed 43.81 g of the aqueous solution containing 18.85% by weight of the choline carbonate or the choline bicarbonate of a high purity without containing by-products obtained as a condensed solution ($5.00 \times 10^{-2}$ mol as the choline bicarbonate), and into the cathode chamber was fed 50 g of ultra-pure water.

The electrolytic reaction was carried out at a temperature of from room temperature to 43° C., at a constant-current density of 10.4 $A/dm^2$ and an electrolyzing voltage of from 12 to 14 V.

As a result of the electrolytic reaction, there were obtained 31.21 g of the aqueous solution containing 2.81% by weight of the choline carbonate and/or the choline bicarbonate of a high purity ($0.53 \times 10^{-2}$ mol as the choline bicarbonate) in the anode chamber and 49.81 g of the aqueous solution containing 10.71% by weight of the choline ($4.40 \times 10^{-2}$ mols) of a high purity in the cathode chamber.

The aqueous solution of the choline of a high purity obtained in the cathode chamber contained by-products at concentrations that were smaller than a detectable limit, and contained 7 ppb of Fe, smaller than 5 ppb of Ni and Cr, and smaller than 10 ppb of Cl.

Comparative Example 1

The aqueous solution of the choline carbonate or the choline bicarbonate to be used for the electrolysis was prepared as described below.

The carbon dioxide gas was blown into the aqueous solution containing 47.68% by weight of the choline and further containing 1.82% by weight of by-products with respect to the chlorine. The aqueous solution was then diluted with pure water to obtain an aqueous solution containing 40.22% by weight of the chlorine carbonate and/or the choline bicarbonate and further containing 1.54% by weight of carbonate and/or bicarbonate of the by-product with respect to the choline carbonate or the choline bicarbonate, which was then subjected to the electrolytic reaction described below.

The electrolytic cell was the same as that of Example 1.

Into the anode chamber was fed 50.00 g of the aqueous solution containing 40.22% by weight of the choline carbonate and/or the choline bicarbonate and containing 1.54% by weight of carbonate and/or bicarbonate of the by-product with respect to the choline carbonate or the choline bicarbonate ($12.17 \times 10^{-2}$ mols as the choline bicarbonate), and into the cathode chamber was fed 50.00 g of the aqueous solution containing 3.75% by weight of the choline but without containing by-products ($1.55 \times 10^{-2}$ mols).

The batchwise electrolysis was carried out at a temperature of from room temperature to 29° C., a constant-current density of 7.6 $A/dm^2$ and an electrolyzing voltage of from 10 to 12 V for 5 hours.

As a result of the electrolytic reaction, there were obtained 39.96 g of the aqueous solution containing 32.86% by weight of the choline carbonate and/or the choline bicarbonate ($7.95 \times 10^{-2}$ mols as the choline bicarbonate) in the anode chamber and 58.09 g of the aqueous solution containing 11.63% by weight of the choline ($5.58 \times 10^{-2}$ mols) in the cathode chamber.

The aqueous solution of the choline obtained in the cathode chamber contained by-products in an amount of 1.22% by weight with respect to the choline.

According to the present invention, an aqueous choline solution not containing by-products and having a high purity can be obtained by process consisting of the following steps:

reacting an aqueous choline solution containing by-products, which are an ethylene oxide aduct of the choline, with a host molecule such as 1,1'-bis-naphtol to produce a choline inclusion complex not containing by-products;

reacting the choline inclusion complex with a carbon dioxide gas to produce an aqueous solution of a choline carbonate or bicarbonate which has a high purity; and electrolyzing the aqueous solution of a choline carbonate or choline bicarbonate by using a cation-exchange membrane as a diaphragm.

The choline that is obtained is a strongly basic compound having a high purity and is very useful as a photoresist-developing solution.

We claim:

1. A method of producing a choline of a high purity, wherein a choline carbonate and/or a choline bicarbonate of a high purity obtained by reacting a molecule-inclusion complex of the chlorine with a carbon dioxide gas, is subjected to an electrolysis using a cation-exchange membrane as a diaphragm.

2. A method according to claim 1, wherein the choline carbonate or the choline bicarbonate of a high purity is fed to an anode chamber, and the choline of a high purity is taken out of a cathode chamber that is separated to the anode chamber by the cation-exchange membrane.

3. A method according to claim 1, wherein a molecule-inclusion complex of the choline contains the choline as guest molecules and 1,1'-bis-β-naphthol as host molecules.

4. A method of producing a choline of a high purity, wherein an aqueous solution of the choline containing by-products is reacted with 1,1'-bis-β-naphthol, and a molecule-inclusion complex of the choline that is formed is reacted with a carbon dioxide gas to form a choline carbonate and/or a choline bicarbonate of a high purity, which is then subjected to an electrolysis using a cation-exchange membrane as a diaphragm.

5. A method according to claim 2, wherein a molecule-inclusion complex of the choline contains the choline as guest molecules and 1,1'-bis-naphthol as host molecules.

* * * * *